United States Patent [19]

Kübbeler et al.

[11] 4,351,972
[45] Sep. 28, 1982

[54] PROCESS FOR MAKING ANHYDROUS ALKYL IODIDES

[75] Inventors: Hans K. Kübbeler, Swisttal; Heinz Erpenbach, Cologne; Klaus Gehrmann; Klaus Schmitz, both of Erftstadt, all of Fed. Rep. of Germany

[73] Assignee: Hoechst Aktiengesellschaft, Fed. Rep. of Germany

[21] Appl. No.: 296,328

[22] Filed: Aug. 26, 1981

[30] Foreign Application Priority Data

Sep. 1, 1980 [DE] Fed. Rep. of Germany ....... 3032853

[51] Int. Cl.$^3$ .............................................. C07C 19/02
[52] U.S. Cl. .................................. 570/101; 570/252; 570/253; 570/254; 570/258; 570/261
[58] Field of Search .............. 570/101, 252, 253, 254, 570/258, 261

[56] References Cited

U.S. PATENT DOCUMENTS

| | | | |
|---|---|---|---|
| 2,899,471 | 8/1959 | Huber et al. | 570/101 X |
| 3,657,365 | 4/1972 | Fernholz et al. | 570/101 |
| 3,784,518 | 1/1974 | Pawlik | 570/195 X |
| 4,302,432 | 11/1981 | Polichnowski | 570/101 X |

FOREIGN PATENT DOCUMENTS

| | | | |
|---|---|---|---|
| 2211231 | 3/1973 | Fed. Rep. of Germany | 570/101 |
| 2450965 | 4/1976 | Fed. Rep. of Germany | 570/101 |
| 2610036 | 9/1976 | Fed. Rep. of Germany | 570/101 |
| 2836084 | 3/1980 | Fed. Rep. of Germany | 570/101 |

*Primary Examiner*—Robert V. Hines
*Attorney, Agent, or Firm*—Connolly and Hutz

[57] ABSTRACT

The invention relates to the production of anhydrous alkyl iodides. To this end, carboxylic acid alkyl esters of the formula $R^1COOR^2$, in which $R^1$ stands for hydrogen or an alkyl or aryl radical having from 1 to 8 carbon atoms and $R^2$ stands for an alkyl group having from 1 to 4 carbon atoms, are reacted with iodine and hydrogen and optionally with carbon monoxide in the presence of compounds of noble metals comprised of rhodium, iridium, palladium or ruthenium as catalyst, and of a heterocyclic aromatic compound, in which at least one hetero atom is a quaternary nitrogen atom, or of a quaternary organophosphorus compound as a promoter, and optionally also in the presence of a carboxylic acid having from 1 to 8 carbon atoms and/or its anhydrides. The reaction is effected under practically anhydrous conditions at temperatures of from 350 to 420 K. and under a total pressure of up to 30 bars.

4 Claims, No Drawings

PROCESS FOR MAKING ANHYDROUS ALKYL IODIDES

Anhydrous alkyl iodides are frequently used in preparative organic chemistry for carrying out alkylation reactions. More recently, anhydrous alkyl iodides, especially methyl iodide, have also found commercial use; in the process described in DE-OS No. 2 610 036 for making acetic anhydride from methyl acetate, it is invariably necessary, for example, for anhydrous CH$_3$I to be used.

The processes described heretofore for the manufacture of alkyl iodides are either effected in an aqueous medium or water is being formed during alkyl iodide manufacture. U.S. Pat. No. 3,748,518, for example, discloses the preparation of alkyl iodides such as CH$_3$I, from alkanols, such as CH$_3$OH, with the use of iodine and hydrogen in contact with Rh-catalysts in gas phase in accordance with the following equation:

$$2CH_3OH + H_2 + I_2 \rightarrow 2CH_3I + 2H_2O$$

A further process for making alkyl iodides, especially CH$_3$I, in aqueous solution by reacting CH$_3$OH with iodine and CO in contact with rhodium or iridium catalysts in accordance with the following overall equation:

$$2CH_3OH + I_2 + CO \rightarrow 2CH_3I + CO_2 + H_2O$$

has been described in DE-OS No. 22 11 231.

These processes suffer from the disadvantage that it is necessary for the alkyl iodide to be first carefully separated from water for later use under anhydrous conditions. In other words, it is necessary for CH$_3$I to be made in an anhydrous medium without formation of reaction water.

The present invention now provides a process for making anhydrous alkyl iodides, which comprises: reacting carboxylic acid alkyl esters of the formula R$^1$COOR$^2$, in which R$^1$ stands for hydrogen or an alkyl or aryl radical having from 1 to 8 carbon atoms and R$^2$ stands for an alkyl group having from 1 to 4 carbon atoms, with iodine and hydrogen and optionally carbon monoxide in the presence of compounds of noble metals comprised of rhodium, iridium, palladium or ruthenium as catalysts and of a heterocyclic aromatic compound, in which at least one hetero atom is a quaternary nitrogen atom, or of a quaternary organophosphorus compound as a promoter, and optionally also in the presence of carboxylic acids having from 1 to 8 carbon atoms and/or their anhydrides, the reaction being effected under practically anhydrous conditions at temperatures of from 350 to 420 K and under a total pressure of up to 30 bars.

The present process occurs as shown by the following overall equation:

$$I_2 + 2R^1COOR^2 + H_2 \rightarrow 2R^1COOH + 2R^2I$$

Further preferred features which can be used individually or in combination provide:
(a) for the heterocyclic compounds or organophosphorus compounds to be used in the form of their addition products with acetic acid or methyl iodide;
(b) for the catalyst system comprised of noble metal compound/promoter/carboxylic acid (-anhydride) to be used in a molar ratio of 1:(5-500):(0-700); and
(c) for hydrogen/carbon monoxide mixtures containing up to 35 volume % of carbon monoxide to be used.

The heterocyclic aromatic compounds and quaternary organo-phosphorus compounds which are used in the process of this invention may be selected, for example, from the following:
(1) N-methylpyridinium iodide, N,N-dimethylimidazolium iodide, N-methyl-3-picolinium iodide, N-methyl-2,4-lutidinium iodide, N-methyl-3,4-lutidinium iodide, N-methyl-quinolinium iodide;
(2) pyridinium acetate, N-methylimidazolium acetate, 3-picolinium acetate, 2,4-lutidinium acetate, 3,4-lutidinium acetate;
(3) tributyl-methyl-phosphonium iodide, trioctyl-methyl-phosphonium iodide, trilauryl-methyl-phosphonium iodide, triphenyl-methyl-phosphonium iodide.

The anhydrous alkyl iodide, i.e. CH$_3$I, obtained in the present process is easy to separate from the reaction product by distillation. After replacement, in the reaction solution, of the proportions of iodine and carboxylic acid alkyl ester which underwent conversion, it is possible for the solution to be used again in the reaction cycle. It is also possible however for the reaction solution with the CH$_3$I therein to be directly employed in the process for making acetic anhydride from methyl acetate and carbon monoxide, described in DE-OS Nos. 24 50 965 and 28 36 084, respectively. It is inversely possible for the catalyst solution used in the manufacture of acetic anhydride to be employed, after admixture of iodine and methyl acetate, for making CH$_3$I in accordance with this invention.

In the process of this invention, it is necessary to bring the hydrogen and optionally carbon monoxide into intimate contact with the reaction solution. To this end, a nozzle should conveniently be used for introducing the gas or gas mixture into the reaction solution which may additionally be stirred, if desired.

The total pressure should preferably not exceed 30 bars. The hydrogen partial pressure may be as high as 20 bars. CO-partial pressure values of more than 10 bars could not be found favorably to influence the desirable reaction. The noble metal should conveniently be used in proportions within the range 0.0001 to 0.01 mol per mol carboxylic acid alkyl ester.

EXAMPLE 1

1.2 g [Rh(CO)$_2$Cl]$_2$ in 250 g methyl acetate and 50 g acetic acid were placed in a pressure vessel of stainless steel and admixed therein with 60 g N,N-dimethylimidazolium iodide. 50 g iodine was added, CO was admitted under a pressure of 2 bars and hydrogen was admitted under a pressure of 4 bars. Next, the whole was heated for 58 minutes with agitation to 373 K. Gas chromatographic analysis indicated that the reaction mixture contained 55.7 g CH$_3$I. The yield was 99.6% of the theoretical, based on the iodine used.

EXAMPLE 2

5 g PdCl$_2$[P(C$_6$H$_5$)$_3$]$_2$ in 250 g methyl acetate and 50 g acetic acid were placed in a pressure vessel and admixed with 100 g methyltriphenylphosphonium iodide. 50 g iodine was added, CO was admitted under a pressure of 4 bars and hydrogen was admitted under a pressure of 8 bars. The whole was heated for 78 minutes with agitation to 383 K and 55.6 g CH$_3$I was obtained.

EXAMPLE 3

1.9 g [IrCl(CO)$_3$]$_2$ in 250 g methyl acetate and 50 g acetic acid were placed in a pressure vessel and admixed with 65 g N-methyl-3-picolinium iodide. 50 g iodine was added, CO was admitted under a pressure of 2 bars and hydrogen was admitted under a pressure of 4 bars. The whole was heated for 2 hours with agitation to 373 K and 55.7 g CH$_3$I was obtained.

EXAMPLE 4

1.6 g [RuCl$_2$(CO)$_3$]$_2$ in 250 g methyl acetate and 50 g acetic acid were placed in a pressure vessel and admixed with 70 g N,N-dimethylimidazolium iodide. 50 g iodine was added, CO was admitted under a pressure of 4 bars and hydrogen was admitted under a pressure of 8 bars. The whole was heated for 72 minutes with agitation to 393 K. The reaction mixture was found to contain 55.6 g CH$_3$I.

EXAMPLE 5

2 g [Rh(CO)$_2$Cl]$_2$ in 250 g methyl acetate and 60 g acetic anhydride were placed in a pressure vessel and admixed with 70 g N,N-dimethylimidazolium iodide. 100 g iodine was added, CO was admitted under a pressure of 2 bars and hydrogen was admitted under a pressure of 4 bars. The whole was reacted for 83 minutes at 383 K with agitation under pressure of about 10 bars, while hydrogen was admitted. The reaction mixture was analyzed and found to contain 110.3 g CH$_3$I.

EXAMPLE 6

1.8 g [Rh(CO)$_2$Cl]$_2$ in 250 g methyl acetate and 60 g acetic anhydride were placed in a pressure vessel and admixed with 50 g N-methyl-3-picolinium iodide. 100 g iodine was added, hydrogen was admitted under a pressure of 6 bars and the whole was heated to 383 K. After a reaction period of 88 minutes while hydrogen was admitted by means of a gas distributing frit under a pressure of about 10 bars, the reaction mixture was found to contain 110.7 g CH$_3$I.

EXAMPLE 7

50 g catalyst base product originating from the manufacture of acetic anhydride and consisting essentially of N,N-dimethyl imidazolium iodide with 0.15 g Rh therein was admixed in a pressure vessel with 250 g methyl acetate. 100 g iodine was added, hydrogen was admitted under a pressure of 5 bars and the whole was heated to 393 K. The reaction which was effected with agitation and while hydrogen was admitted under a pressure of about 9 bars was terminated after 52 minutes. The reaction mixture was found to contain 111 g CH$_3$I.

EXAMPLE 8

1.5 g [Rh(CO)$_2$Cl]$_2$ in 300 g benzoic acid methylester and 20 g benzoic acid were placed in a pressure vessel and admixed with 60 g N,N-dimethylimidazolium iodide. 50 g iodine was added, CO was admitted under a pressure of 2 bars and hydrogen was admitted under a pressure of 4 bars. Next, the mixture was heated for 40 minutes with agitation to 398 K. The reaction mixture was found to contain 55.3 g CH$_3$I.

EXAMPLE 9

1.2 g [Rh(CO)$_2$Cl]$_2$ in 250 g ethyl propionate and 60 g propionic acid were placed in a pressure vessel and admixed with 60 g N-methyl-3-picolinium iodide and 50 g iodine. CO was admitted under a pressure of 2 bars and hydrogen was admitted under a pressure of 8 bars. Next, the whole was heated for 37 minutes with agitation to 393 K. The reaction mixture was found to contain 60.5 g C$_2$H$_5$I.

EXAMPLE 10

0.1 g [Rh(CO)$_2$Cl]$_2$ in 250 g methyl acetate and 20 g acetic acid were placed in a pressure vessel and admixed with 75 methyl-tributyl-phosphonium iodide. 25 g iodine was added, CO was admitted under a pressure of 4 bars and hydrogen was admitted under a pressure of 8 bars. Next, the whole was heated for 118 minutes with agitation to 393 K. The reaction mixture was found to contain 27.8 g CH$_3$I.

EXAMPLE 11

5.9 g [Rh(CO)$_2$Cl]$_2$ in 250 g methyl acetate and 60 g N,N-dimethylimidazolium iodide were placed in a pressure vessel. 60 g iodine was added, CO was admitted under a pressure of 2 bars and hydrogen was admitted under a pressure of 4 bars. The whole was heated for 28 minutes to 383 K with agitation and while hydrogen was admitted under a pressure of about 10 bars. The reaction product was found to contain 67 g CH$_3$I.

EXAMPLE 12

6 g [Rh(CO)$_2$Cl]$_2$ in 1550 g methyl acetate and 500 g acetic acid were placed in a Hastelloy pressure vessel and admixed with 250 g N,N-dimethylimidazolium iodide. 2500 g iodine was added, CO was admitted under a pressure of 2 bars and hydrogen was admitted under a pressure of 4 bars. Next, the whole was heated to 383 K while further hydrogen was admitted under a total pressure of about 10 bars. The reaction was terminated as soon as analysis indicated that more methane than normal was evolved in the gas chamber. The methyl iodide was obtained distillatively. 2791 g CH$_3$I was obtained. The yield was quantitative. The catalyst base product was admixed with fresh starting material (methyl acetate and iodine) which replaced consumed material and could repeatedly be used without loss of activity for the manufacture of further methyl iodide under identical conditions.

We claim:

1. A process for making anhydrous alkyl iodides, which comprises: reacting carboxylic acid alkyl esters of the formula R$^1$COOR$^2$, in which R$^1$ stands for hydrogen or an alkyl or aryl radical having from 1 to 8 carbon atoms and R$^2$ stands for an alkyl group having from 1 to 4 carbon atoms, with iodine and hydrogen and optionally carbon monoxide in the presence of compounds of noble metals comprised of rhodium, iridium, palladium or ruthenium as catalyst, and of a heterocyclic aromatic compound, in which at least one hetero atom is a quaternary nitrogen atom, or of a quaternary organophosphorus compound as a promoter, and optionally also in the presence of carboxylic acids having from 1 to 8 carbon atoms and/or their anhydrides, the reaction being effected under practically anhydrous conditions at temperatures of from 350 to 420 K and under a total pressure of up to 30 bars.

2. A process as claimed in claim 1, wherein the heterocyclic compounds or organophosphorus compounds are used in the form of their addition products with acetic acid or methyl iodide.

3. A process as claimed in claim 1, wherein the catalyst system comprised of noble metal compound/promoter/carboxylic acid (-anhydride) is used in a molar ratio of 1:(5–500):(0–700).

4. A process as claimed in claim 1, wherein hydrogen/carbon monoxide mixtures containing up to 35 volume % of carbon monoxide are used.

* * * * *